(12) United States Patent
Kovarik

(10) Patent No.: US 12,239,706 B2
(45) Date of Patent: Mar. 4, 2025

(54) METHOD AND SYSTEM FOR PROTECTING MONARCH BUTTERFLIES FROM PESTICIDES

(71) Applicant: Seed Health, Inc., Venice, CA (US)

(72) Inventor: Joseph E. Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 455 days.

(21) Appl. No.: 17/678,840

(22) Filed: Feb. 23, 2022

(65) Prior Publication Data

US 2022/0175914 A1   Jun. 9, 2022

Related U.S. Application Data

(63) Continuation-in-part of application No. 17/185,618, filed on Feb. 25, 2021, now Pat. No. 11,529,412, which is a continuation-in-part of application No. 16/892,623, filed on Jun. 4, 2020, now Pat. No. 10,933,128, which is a continuation-in-part of application No. 16/246,652, filed on Jan. 14, 2019, now Pat. No. 10,675,347, which is a continuation-in-part of application No. 16/139,232, filed on Sep. 24, 2018, now Pat. No. 10,568,916, which is a continuation-in-part of application No. 15/379,579, filed on Dec. 15, 2016, now Pat. No. 10,086,024, said application No. 17/185,618 is a continuation-in-part of application No. 15/270,034, filed on Sep. 20, 2016, now Pat. No. 9,750,802, which is a continuation of application No. 14/954,074, filed on Nov. 30, 2015, now Pat. No. 9,457,077.

(60) Provisional application No. 62/278,046, filed on Jan. 13, 2016, provisional application No. 62/277,571, filed on Jan. 12, 2016.

(51) Int. Cl.
| | |
|---|---|
| *A61K 39/35* | (2006.01) |
| *A61K 9/00* | (2006.01) |
| *A61K 35/74* | (2015.01) |
| *A61K 35/741* | (2015.01) |
| *A61K 35/742* | (2015.01) |
| *A61K 35/745* | (2015.01) |
| *A61K 35/747* | (2015.01) |
| *A61K 39/00* | (2006.01) |
| *A61K 39/39* | (2006.01) |
| *A61K 39/395* | (2006.01) |
| *A61K 45/06* | (2006.01) |
| *C07K 16/00* | (2006.01) |

(52) U.S. Cl.
CPC ............ *A61K 39/35* (2013.01); *A61K 9/0034* (2013.01); *A61K 9/0043* (2013.01); *A61K 9/007* (2013.01); *A61K 35/74* (2013.01); *A61K 35/741* (2013.01); *A61K 35/742* (2013.01); *A61K 35/745* (2013.01); *A61K 35/747* (2013.01); *A61K 39/0008* (2013.01); *A61K 39/39* (2013.01); *A61K 39/395* (2013.01); *A61K 45/06* (2013.01); *C07K 16/00* (2013.01); *A61K 2039/505* (2013.01); *A61K 2039/541* (2013.01); *A61K 2039/544* (2013.01); *A61K 2039/55* (2013.01); *A61K 2039/55583* (2013.01); *A61K 2039/577* (2013.01); *A61K 2039/58* (2013.01); *A61K 2039/70* (2013.01)

(58) Field of Classification Search
None
See application file for complete search history.

(56) References Cited

U.S. PATENT DOCUMENTS

| | | |
|---|---|---|
| 3,178,341 A | 4/1965 | Hamill et al. |
| 3,832,460 A | 8/1974 | Kosti |
| 4,136,162 A | 1/1979 | Fuchs et al. |
| 4,163,777 A | 8/1979 | Mitra |
| 4,687,841 A | 8/1987 | Spilburg et al. |
| 4,720,486 A | 1/1988 | Spilburg et al. |
| 5,002,970 A | 3/1991 | Eby, III |
| 5,158,789 A | 10/1992 | DuRoss |
| 5,719,196 A | 2/1998 | Uhari et al. |
| 5,895,648 A | 4/1999 | Vesely et al. |
| 6,054,143 A | 4/2000 | Jones |
| 6,139,861 A | 10/2000 | Friedman |
| 6,210,699 B1 | 4/2001 | Acharya et al. |
| 6,287,610 B1 | 9/2001 | Bowling et al. |

(Continued)

FOREIGN PATENT DOCUMENTS

| | | |
|---|---|---|
| CN | 103937722 | 7/2014 |
| WO | WO 2010/146405 | 12/2010 |

(Continued)

OTHER PUBLICATIONS

Glavinic et al., "Dietary amino acid and vitamin complex protects honey bee from immunosuppression caused by Nosema ceranae," PLOS One, vol. 12, No. 11, 2017, 18 pages.
Song et al., "Characterization of Selected Lactobacillus Strains for Use as Probiotics," Korean Journal for Food Science of Animal Resources, vol. 35, No. 4, 2015, pp. 551-556.
Arredondo et al., "Lactobacillus kunkeei strains decreased the infection by honey bee pathogens Paenibacillus larvae and Nosema ceranae," Beneficial Microbes, vol. 9, No. 2, Feb. 2018, pp. 279-290.

(Continued)

*Primary Examiner* — Oluwatosin A Ogunbiyi
(74) *Attorney, Agent, or Firm* — Sheridan Ross P.C.

(57) ABSTRACT

A method and system for the treatment of Monarch butterflies (*Danaus plexippus Kluk* (Lepidoptera: Nymphalidae) to protect them from various life-threatening conditions, including the negative effects of various pesticides, provides Monarch butterflies with the ability to assimilate and degrade pesticides such as neonicotinoids and fipronil. Certain embodiments involve the inoculation of flowers by honey bees with desired bacteria that are able to degrade pesticides, such that when Monarch butterflies visit such flowers, they are exposed to such bacteria, transforming the microbiome of the Monarch butterflies so that pesticides can be degraded, thus enhancing the health of the Monarch butterflies.

20 Claims, 3 Drawing Sheets

(56) References Cited

U.S. PATENT DOCUMENTS

| | | |
|---|---|---|
| 6,569,474 B2 | 5/2003 | Clayton et al. |
| 6,599,883 B1 | 7/2003 | Romeo et al. |
| 6,919,373 B1 | 7/2005 | Lam et al. |
| 7,087,249 B2 | 8/2006 | Burrell et al. |
| 7,267,975 B2 | 9/2007 | Strobel et al. |
| 7,820,420 B2 | 10/2010 | Whitlock |
| 7,846,711 B2 | 12/2010 | Boettner et al. |
| 8,349,313 B2 | 1/2013 | Smith et al. |
| 8,383,201 B2 | 2/2013 | Berry et al. |
| 8,481,299 B2 | 7/2013 | Gueniche |
| 8,496,914 B2 | 7/2013 | Bonfiglio |
| 8,585,588 B2 | 11/2013 | Kovarik et al. |
| 8,685,389 B2 | 4/2014 | Baur |
| 8,701,671 B2 | 4/2014 | Kovarik |
| 8,716,327 B2 | 5/2014 | Zhao et al. |
| 8,758,764 B2 | 6/2014 | Masignani et al. |
| 8,815,538 B2 | 8/2014 | Lanzalaco et al. |
| 8,865,211 B2 | 10/2014 | Tazannis et al. |
| 8,951,775 B2 | 2/2015 | Castiel |
| 8,999,372 B2 | 4/2015 | Davidson et al. |
| 9,011,834 B1 | 4/2015 | McKenzie et al. |
| 9,017,718 B2 | 4/2015 | Tan et al. |
| 9,028,841 B2 | 5/2015 | Henn et al. |
| 9,131,884 B2 | 9/2015 | Holmes |
| 9,234,204 B2 | 1/2016 | Qvit-Raz et al. |
| 9,288,981 B2 | 3/2016 | Gandhi et al. |
| 10,086,024 B2 | 10/2018 | Kovarik |
| 10,675,347 B2 | 6/2020 | Kovarik |
| 10,933,128 B2 | 3/2021 | Kovarik |
| 11,529,412 B2 | 12/2022 | Kovarik |
| 2002/0009436 A1 | 1/2002 | Doyle et al. |
| 2002/0022057 A1 | 2/2002 | Battey et al. |
| 2003/0031737 A1 | 7/2003 | Rosenbloom |
| 2003/0124178 A1 | 7/2003 | Haley |
| 2003/0206995 A1 | 11/2003 | Bowling et al. |
| 2004/0096569 A1 | 5/2004 | Barkalow et al. |
| 2004/0120991 A1 | 6/2004 | Gardner et al. |
| 2004/0136923 A1 | 7/2004 | Davidson |
| 2004/0228804 A1 | 11/2004 | Jones et al. |
| 2005/0100559 A1 | 5/2005 | Myatt et al. |
| 2005/0196358 A1 | 9/2005 | Georglades et al. |
| 2006/0035008 A1 | 2/2006 | Virgallito et al. |
| 2006/0204591 A1 | 9/2006 | Burrell et al. |
| 2007/0054008 A1 | 3/2007 | Clayton et al. |
| 2007/0207955 A1 | 9/2007 | Tanihara et al. |
| 2007/0218114 A1 | 9/2007 | Duggan |
| 2007/0293587 A1 | 12/2007 | Haley |
| 2008/0080362 A1 | 10/2008 | Dussia |
| 2008/0267933 A1 | 10/2008 | Ohlson et al. |
| 2009/0196907 A1 | 8/2009 | Bunick et al. |
| 2009/0196908 A1 | 8/2009 | Lee |
| 2009/0205083 A1 | 8/2009 | Gupta et al. |
| 2010/0029832 A1 | 2/2010 | Pinnavaia et al. |
| 2010/0285098 A1 | 11/2010 | Haley |
| 2011/0142942 A1 | 6/2011 | Schobel et al. |
| 2011/0217368 A1 | 9/2011 | Prakash et al. |
| 2011/0269119 A1 | 11/2011 | Hutchinson et al. |
| 2012/0027786 A1 | 2/2012 | Gupta |
| 2012/0058094 A1 | 3/2012 | Blasser et al. |
| 2012/0142548 A1 | 6/2012 | Corsi et al. |
| 2012/0276143 A1 | 11/2012 | O'Mahony et al. |
| 2012/0276525 A1 | 11/2012 | Kovarik et al. |
| 2013/0064796 A1 | 3/2013 | Hamdi |
| 2013/0157876 A1 | 6/2013 | Lynch et al. |
| 2013/0259834 A1 | 10/2013 | Klaenhammer et al. |
| 2013/0315869 A1 | 11/2013 | Qimron et al. |
| 2014/0044677 A1 | 2/2014 | Qvit-Raz et al. |
| 2014/0044734 A1 | 2/2014 | Sverdlov et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0068797 A1 | 3/2014 | Doudna et al. |
| 2014/0036849 A1 | 5/2014 | Bryan |
| 2014/0154290 A1 | 6/2014 | Peters et al. |
| 2014/0199266 A1 | 7/2014 | Park et al. |
| 2014/0199281 A1 | 7/2014 | Henn et al. |
| 2014/0212520 A1 | 7/2014 | Del Vecchio et al. |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0038594 A1 | 2/2015 | Borges et al. |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0329555 A1 | 11/2015 | Liras et al. |
| 2015/0329875 A1 | 11/2015 | Gregory et al. |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0024510 A1 | 1/2016 | Bikard et al. |
| 2016/0040216 A1 | 2/2016 | Wilder |
| 2016/0089315 A1 | 3/2016 | Kleinberg et al. |
| 2016/0151427 A1 | 6/2016 | Whitlock et al. |
| 2016/0168594 A1 | 6/2016 | Zhang et al. |
| 2016/0206668 A1 | 7/2016 | Kort et al. |
| 2016/0271106 A1 | 9/2016 | Shi et al. |
| 2016/0271189 A1 | 9/2016 | Cutcliffe |
| 2016/0314281 A1 | 10/2016 | Apte |
| 2016/0348120 A1 | 12/2016 | Esvelt et al. |
| 2016/0354416 A1 | 12/2016 | Gajewski et al. |
| 2017/0020932 A1 | 1/2017 | Cutcliffe et al. |
| 2017/0021011 A1 | 1/2017 | Kovarik et al. |
| 2017/0035820 A1 | 2/2017 | Stamets et al. |
| 2017/0071986 A1 | 3/2017 | Kovarik et al. |
| 2018/0020678 A1 | 1/2018 | Scharf et al. |
| 2018/0119132 A1 | 5/2018 | Hutchinson et al. |
| 2018/0177160 A1 | 6/2018 | Wagoner et al. |
| 2018/0216123 A1 | 8/2018 | Anand et al. |
| 2019/0015528 A1 | 1/2019 | Moran et al. |
| 2019/0022151 A1 | 1/2019 | Kovarik |
| 2019/0177807 A1 | 6/2019 | Wan et al. |
| 2019/0321417 A1 | 10/2019 | Brucker et al. |
| 2020/0318139 A1 | 10/2020 | Gersbach et al. |
| 2022/0211777 A1 | 7/2022 | Kovarik |

FOREIGN PATENT DOCUMENTS

| | | |
|---|---|---|
| WO | WO-2011138310 A2 | 11/2011 |
| WO | WO-2013026000 | 2/2013 |
| WO | WO-2017/040343 | 3/2017 |
| WO | WO 2018/140479 | 8/2018 |

OTHER PUBLICATIONS

Borges, "Control of the Intestinal Parasite Nosema ceranae in Apis mellifera using nutraceuticals, prebiotics and probiotics," A Thesis presented to The University of Guelph in partial fulfilment of the requirements for the degree of Master of Science in Environmental Sciences, Guelph, Ontario, Canada, Sep. 2015, 241 pages.

Bustin et al., "The MIQE Guidelines: Minimum Information for Publication of Quantitative Real-Time PCR Experiments," Clinical Chemistry, vol. 55, No. 4, 2009, pp. 611-622.

Callahan et al., "Exact sequence variants should replace operational taxonomic units in marker-gene dtaa analysis," The ISME Journal, vol. 11, No. 12, Jul. 21, 2017, pp. 2639-2643.

Chmiel et al., "Understanding the Effects of Sublethal Pesticide Exposure on Honey Bees: A Role for Probiotics as Mediators of Environmental Stress," Frontiers In Ecology and Education, vol. 8, No. 22, Feb. 2020, 19 pages.

(56) References Cited

OTHER PUBLICATIONS

Daisley et al., "Microbiota-Mediated Modulation of Organophosphate Insectide Toxicity by Species-Dependent Interactions with Lactobacilli in a *Drosophila melanogaster* Insect Model," Applied and Environmental Microbiology, vol. 84, No. 9, May 2018, 13 pages.

Daisley et al., "Neonicotinoid-induced pathogen susceptibility is mitigated by Lactobacillus plantarum immune stimulation in a *Drosophila melanogaster* model," Scientific Reports, vol. 7, No. 2703, Jun. 2, 2017, 13 pages.

Daisley et al., "Novel probiotic approach to counter Paenibacillus larvae infection in honey bees," The ISME Journal, vol. 14, Oct. 29, 2019, pp. 476-491.

De Graaf et al., "Standard methods for American foulbrood research," Journal of Applied Agricultural Research, vol. 52, No. 1, 2013, 29 pages.

Degrandi-Hoffman et al., "Comparisons of pollen substitute diets for honey bees: consumption rates by colonies and effects on brood and adult populations," Journal of Agricultural Research and Bee World, vol. 74, No. 4, 2008, pp. 265-270.

Gloor et al., "Compositional analysis: a valid approach to analyse microbiome high-throughput sequencing data." Canadian Journal of Microbiology, vol. 62, Apr. 2016, pp. 692-703.

Harpur et al., "No Genetic Tradeoffs between Hygienic Behaviour and Individual Innate Immunity in the Honey Bee, Apis mellifera," PLoS One, vol. 9, No. 8, Aug. 2014, 7 pages.

Irandoust et al., "Nutritional Effects of High Protein Feeds on Growth, Development, Performance and Overwintering of Honey Bee (*Apis mellifera* L.)," International Journal of Advanced Biological and Biomedical Research, vol. 1, No. 6, 2013, pp. 601-613.

Newton et al., "The effect of training set on the classification of honey bee gut microbiota using the Naïve Bayesian Classifier," BMC Microbiology, vol. 12, Dec. 2012, 9 pages.

Okuyama et al., "The complete mitochondrial genome of a Buckfast bee, *Apis mellifera* (Insecta: Hymenoptera: Apidae) in Northern Ireland," Mitochondrial DNA Part B: Resources, vol. 3, No. 1, Jan. 2018, pp. 338-339.

Powell et al., "Routes of Acquisition of the Gut Microbiota of the Honey Bee *Apis mellifera*," Applied and Environmental Microbiology, vol. 80, No. 23, Dec. 2014, pp. 7378-7387.

Rangberg et al., "The Paratransgenic Potential of Lactobacillus kunkeei in the Honey Bee *Apis mellifera*," Beneficial Microbes, vol. 6, No. 4, Feb. 2015, pp. 513-523.

Shimanuki et al., "Diagnosis of Honey Bee Diseases," United States Department of Agriculture Agricultural Research Service, Agricultural Handbook No. 690, issued Apr. 1991, revised Jul. 2000, 63 pages.

Smart et al., "Linking Measures of Colony and Individual Honey Bee Health to Survival among Apiaries Exposed to Varying Agricultural Land Use," PLoS One, vol. 11, No. 3, Mar. 30, 2016, 28 pages.

Standifer et al., "Supplemental Feeding of Honey Bee Colonies," United States Department of Agriculture Science and Education Administration, Agriculture Information Bulletin No. 413, Jun. 1978, 12 pages.

Trinder et al., "Probiotic Lactobacillus rhammosus Reduces Organophosphate Pesticide Absorption and Toxicity to *Drosophila melanogaster*," Applied and Environmental Microbiology, vol. 82, No. 20, Oct. 2016, pp. 6204-6213.

Vanengelsdorp et al., "Colony Collapse Disorder: A Descriptive Study," PLoS One, vol. 4, No. 8, Aug. 2009, 17 pages.

Vasquez et al., "Symbionts as Major Modulators of Insect Health: Lactic Acid Bacteria and Honeybees," PLoS One, vol. 7, No. 3, Mar. 2012, 9 pages.

Versalovic et al., "Genomic Fingerprinting of Bacteria Using Repetitive Sequence-Based polymerase Chain Reaction," Methods in Molecular and Cellular Biology, vol. 5, 1994, pp. 25-40.

Wang et al., "Bacterial Genome Editing with CRISPR-Cas9: Deletion, Integration, Single Nucleotide Modification, and Desirable "Clean" Mutant Selection in Clostridium beijerinckii as an Example," ACS Synthetic Biology, vol. 5, Apr. 2016, pp. 721-732.

International Search Report and Written Opinion for International (PCT) Patent Application No. PCT/US2019/047059, dated Mar. 24, 2020, 13 pages.

International Preliminary Report on Patentability for International (PCT) Patent Application No. PCT/US2019/047059, dated Mar. 4, 2021, 10 pages.

Team British Columbia, Probeeotics UBC Igem 2015, pp. 1-46.

Team British Columbia, Welcome to the UBC Igem Wiki. pages 1-4, http://2015.igem.org/Team: British_Columbia.

Zhai, et al., Molecular cloning, purification and biochemical characterization of a novel pyrethroid-hydrolyzing carboxylesterase gene from *Ochrobactrum anthropi* YZ-1, Journal of Hazardous Materials, Jun. 2012, pp. 206-212.

P.C. Wu, Y.H. Liu, Z.Y. Wang, X.Y. Zhang, H. Li, W.Q. Liang, N. Luo, J.M. Hu, J.Q. Lu, T.G. Luan, L.X. Cao Molecular cloning, purification, and biochemical characterization of a novel pyrethroid-hydrolyzing esterase from *Klebsiella* sp. strain ZD112, J. Agric. Food Chem., 54 (2006), pp. 836-842.

B.Z. Wang, P. Guo, B.J. Hang, L. Li, J. He, S.P. Li Cloning of a novel pyrethroid-hydrolyzing carboxylesterase gene from *Sphingobium* sp. JZ-1 and characterization of the gene product; Appl. Environ. Microbiol., 75 (2009), pp. 5496-5500.

G. Li, K. Wang, Y.H. Liu Molecular cloning and characterization of a novel pyrethroid-hydrolyzing esterase originating from the metagenome; Microb. Cell Factories, 7 (2008).

S Pankaj, S Gangola, P Khati, G Kumar, A Srivastava—Novel pathway of cypermethrin biodegradation in a *Bacillus* sp. strain SG2 isolated from cypermethrin-contaminated agriculture field; 3 Biotech, 2016—ncbi.nlm.nih.gov.

H Itoh, K Tago, M Hayatsu, Y Kikuchi—Natural product reports, 2018; Detoxifying symbiosis: microbe-mediated detoxification of phytotoxins and pesticides in insects;—pubs.rsc.org.

T Gong, X Xu, Y Dang, A Kong, Y Wu, P Liang . . . An engineered *Pseudomonas putida* can simultaneously degrade organophosphates, pyrethroids and carbamates—Science of The Total . . . , 2018—Elsevier.

Smith et al., bioRxiv preprint (Jul. 11, 2018), Genomic signatures of honey bee association in an acetic acid symbiont.

Huang et al., Genome Sequencing and Comparative Analysis of Stenotrophomonas acidaminiphila, Reveal Evolutionary Insights Into Sulfamethoxazole Resistance, Front Microbiol. 2018; 9: 1013.

Degradation of fipronil by Stenotrophomonasacidaminiphila, Uniyal, et al., Degradation of fipronil by Stenotrophomonasacidaminiphila isolated from rhizospheric soil of *Zea mays*, 3 Biotech. Jun. 2016; 6(1): 48.

Mandal K, et al, Microbial degradation of fipronil by Bacillus thuringiensis, Ecotoxicol Environ Saf. Jul. 2013; 93:87-92.

Medhi, et. al, Genome Sequence of a Heterotrophic Nitrifier and Aerobic Denitrifier, *Paracoccus denitrificans* Strain ISTOD1, Isolated from Wastewater, Genome Announc. Apr. 2018; 6(15):e00210-18.

Kumar et al., Biodegradation of Fipronil by *Paracoccus* sp in Different Types of Soil, Bulletin of Environmental Contamination and Toxicology 88(5):781-7 (2012).

CRISPR/Cas9 & Targeted Genome Editing: New Era in Molecular Biology https://www.neb.com/tools-and-resources/feature-articles/crispr-case9-and-targeted-genome-editing-a-new-era-in-molecular-biology retrieved Aug. 22, 2019.

Smith et al. Genomic Signatures of Honey Bee Association in an Acetic Acid Symbiont, Genome Biol. Evol. 12(10: 1882-1894.

METHOD AND SYSTEM FOR PROTECTING MONARCH BUTTERFLIES FROM PESTICIDES

RELATED APPLICATIONS

This application is a continuation-in-part of U.S. patent application Ser. No. 17/185,618, filed Feb. 25, 2021, (now U.S. Pat. No. 11,529,412, issued Dec. 20, 2022), which is a continuation-in-part of U.S. patent application Ser. No. 16/892,623, filed Jun. 4, 2020 (now U.S. Pat. No. 10,933,128, issued Mar. 2, 2021), which is a continuation-in-part of U.S. patent application Ser. No. 16/246,652, filed Jan. 14, 2019 (now U.S. Pat. No. 10,675,347, issued Jun. 9, 2020), which is a continuation-in-part application of U.S. patent application Ser. No. 16/139,232, filed Sep. 24, 2018 (now U.S. Pat. No. 10,568,916, issued Feb. 25, 2020), which is a continuation-in-part application of U.S. patent application Ser. No. 15/379,579, filed Dec. 15, 2016 (now U.S. patent Ser. No. 10/086,024, issued Oct. 2, 2018), which claims priority from U.S. Provisional Patent Application Ser. No. 62/277,568, filed on Jan. 12, 2016, from U.S. Provisional Patent Application Ser. No. 62/277,571, filed on Jan. 12, 2016 and U.S. Provisional Patent Application Ser. No. 62/278,046, filed on Jan. 13, 2016.

This application also is a continuation-in-part of U.S. patent application Ser. No. 15/270,034, filed on Sep. 20, 2016 (now U.S. Pat. No. 9,750,802, issued Sep. 5, 2017, which is a continuation of U.S. patent application Ser. No. 14/954,074, filed on Nov. 30, 2015 (now U.S. Pat. No. 9,457,077, issued Oct. 4, 2016).

The entire disclosure of the prior applications are considered to be part of the disclosure of the accompanying application and are hereby incorporated by reference.

FIELD OF THE INVENTION

The present invention relates to a method and system for the treatment of Monarch butterflies and is directed to providing such butterflies with the ability to assimilate and degrade pesticides, including neonicotinoids and fipronil.

BACKGROUND OF THE INVENTION

The annual migration of North America's monarch butterfly (*Danaus plexippus Kluk* (Lepidoptera: Nymphalidae) is a unique and amazing phenomenon. The monarch is the only butterfly known to make a two-way migration as birds do. Unlike other butterflies that can overwinter as larvae, pupae, or even as adults in some species, monarchs cannot survive the cold winters of northern climates. Using environmental cues, the monarchs know when it is time to travel south for the winter. Monarchs use a combination of air currents and thermals to travel long distances. Some fly as far as 3,000 miles to reach their winter home. The multi-generational migration of North American monarch butterflies between breeding grounds in the northern U.S. and southern Canada and wintering grounds in central Mexico and coastal California is one of the world's most spectacular natural events. The interest in monarchs and their fascinating, visible biology is demonstrated by monarch butterflies being the official insect or butterfly of seven U.S. states; celebrated via festivals in Mexico, the United States, and Canada; the focus of science curricula; and the subject of multiple citizen-science projects.

Monarch butterfly populations have declined precipitously in North America in the last twenty years. This decline has commonly been linked to loss of milkweeds (*Asclepias* species) from farmer's fields. Monarch caterpillars are dependent on milkweeds. The ability of farmers to kill them with the Monsanto herbicide Roundup (glyphosate) has therefore led to this herbicide being considered as a major contributor to the decline of the monarch butterfly. Adult monarch butterflies feed on nectar that provides sugars and other nutrients. Monarch butterflies migrate to Mexican forests for overwintering. Overwintering monarchs reduce their metabolism and limit their feeding.

The introduction of neonicotinoids into the agricultural marketplace occurred around the same time as the introduction of GMO crops in the mid-to-late 1990s. Monsanto and Syngenta, the undisputed leaders in patented genetically engineered seeds, also have close relationships with the leading global neonic producer, Bayer. Most new commodity crops are increasingly coming to farmers with stacked traits, which means more than one transgenic alteration. These genetically engineered and transplanted traits are marketed to farmers as providing benefits such as resistance to multiple herbicides, pests, funguses, heat and drought.

Seed treatment applications are prophylactic, meaning they are used whether or not there is any evidence of pest pressures. At least 30 percent of soybean seeds planted annually (approximately 22.5 million out of 75 million acres) are pretreated with neonic insecticides (two of the primary four being imidacloprid and thiamethoxam). But corn has the highest use and acreage with around 94 percent of U.S. corn treated with a neonicotinoid. That widespread use has quickly elevated the Midwest to the highest levels of neonicotinoid use in the country. These neonicotinoids don't stay in the plants and soil however, but find their ways into the water as well. A recent U.S. Geological Survey report confirmed that neonicotinoids were common in streams throughout the Midwest.

In 1999, common milkweed, the monarch's food plant, was found in half of corn and soybean fields, but in only 8% of them a decade later. Glyphosatetolerant GM crops are grown in the same fields each year. Once absorbed, glyphosate is translocated to the roots and therefore the milkweed does not regenerate. The monarch life cycle begins each spring when it deposits eggs on milkweed leaves. In the branches of Oyamel fir trees mountains above Mexico City, hundreds of millions of hibernating monarch butterflies reside for winter months. Each February, the monarchs begin a mass migration north, most crossing over the Rio Grande into Texas and once there, they mate, lay eggs and die. The eggs are considered the first generation of the year. In mid-March, they hatch as a caterpillar and after 2-3 weeks, they form a chrysalis, transforming into a butterfly about 10 days thereafter. Most of the first generation, which will only live 4-6 weeks, head north to northeast, where they also mate, lay eggs and die. A second generation then hatches, flies further north to around Ontario by June and then dies after mating and laying eggs. A third generation is thereafter hatched and matures in the same timeframe, but remain within the same general area for their 4-6 week lifespan. Finally, a fourth generation hatch and mature. In August, this fourth generation, without mating, head south back to the mountains of Central Mexico.

The monarch butterfly evolved closely alongside the milkweed—a toxic plant named for the sticky white substance emitted when its leaves are damaged that is the only food source for monarch caterpillars. Notably, there are no milkweed plants in the region where monarch butterflies hibernate. But without the milkweed, the butterflies cannot survive. Milkweed emerges and matures in Texas by March, in May grows in the northern states, corresponding with the second monarch generation, and grows in Canada just in time for the second generation to arrive there and lay eggs for Generation Three.

Female Monarch caterpillars will only lay their eggs on one milkweed not-already-occupied plant because another monarch caterpillar will eat a monarch egg. Thus, hundreds of millions of milkweed are necessary to sustain a population of hundreds of millions of monarchs.

The sap of the milkweed contains toxins that become sequestered within the body of the monarch, making the insect toxic to other predators—like birds. During the return journey to Mexico, Monarchs feed on nectar from almost any nectar-producing flower they come across. Thus, although the early life stages of a monarch are dependent on milkweed, adults require nectar from a wide diversity of plants, especially late season blooms.

It has been shown that clothianidin, a very long-acting systemic neonicotinoid insecticide, has contributed to the decline of monarch butterflies. USDA researchers have identified the neonicotinoid insecticide clothianidin as a likely contributor to monarch butterfly declines in North America. Neonicotinoids have been strongly implicated in pollinator declines worldwide. As shown by a report from a task force of the International Union of Nature Conservation based in Switzerland, neonicotinoids, such as clothianidin (Bayer), are a particular hazard because, unlike most pesticides, they are soluble molecules. From soil or seed treatments they can reach nectar and are found in pollen.

USDA researchers have shown that clothianidin can have effects on monarch caterpillars at doses as low as 1 part per billion. The effects seen in experiments were on caterpillar size, caterpillar weight, and caterpillar survival. The lethal dose (LC50) they found to be 15 parts per billion. The caterpillars in their experiments were exposed to clothianidin-treated food for only 36 hours, however. The researchers therefore noted that in agricultural environments caterpillar exposure would likely be greater than in their experiments. Furthermore, that butterfly caterpillars would be exposed in nature to other pesticides, including other neonicotinoids. In sampling experiments from agricultural areas in South Dakota the researchers found that milkweeds had on average over 1 ppb clothianidin. On this basis the USDA researchers concluded that "neonicotinoids could negatively affect larval monarch populations."

Neonicotinoids are now the most widely used pesticides in the world. Neonicotinoids are neurotoxins that are partially banned in the EU. There has been negligible research on the effects of neonicotinoids on butterflies. There is a desperate need for an effective treatment to advert the destruction of monarch butterflies that has been observed over the last decade. The ramifications of the elimination of the monarch butterfly will have tremendous and as yet unforeseen negative effects on the environment. A need for a treatment is therefore long felt and unsolved. The present invention is directed to a method and system that achieves this objective.

SUMMARY OF THE INVENTION

One aspect of the present invention is directed to addressing how to stem the tide of butterfly decline, and in particular Monarch butterfly declines, by modifying the gut microbiota of monarch butterflies so as to enable the butterflies to degrade neonicotinoids, thus providing a method and system to assist in the survival and reproduction of the monarch butterfly. Herein after, while emphasis is placed on Monarch butterflies, one of skill in the art will appreciate the application of the present invention to other pollinators, such as other butterflies, moths, etc. Monarch butterflies frequently consume milkweed in and near agroecosystems and consequently may be exposed to pesticides like neonicotinoids. One aspect of the present invention is directed to addressing how to stem the tide of monarch butterfly decline by modifying the gut microbiota of monarch butterflies so as to enable the butterflies to degrade neonicotinoids, thus providing a method and system to assist in the survival and reproduction of the monarch butterfly.

Numerous genes (both host and symbiont) and the proteins or contigs they encode are identified herein as being associated with nicotinoid-pathogen synergy, as further described in US patent publication no. 20180020678, incorporated herein by this reference. By regulating the expression of one or more of these identified genes, proteins, and/or contigs, e.g. via the use of CRISPR-systems, the nicotinoid degradation can proceed to render the hosts (honey bees, bats, butterflies, etc.) less susceptible to nicotinoids.

Fipronil [5-Amino-3-cyano-1-(2,6-dichloro 4 trifluoromethylphenyl)-4-trifluoromethyl sulfinyl pyrazole is a phenyl pyrazole insecticide first synthesized by Rho{circumflex over ( )}ne Poulenc Ag Company (now Bayer Crop Science) in 1987, introduced for use in 1993 and registered in the U.S. in 1996. Fipronil is labeled for use in large number of crops and is effective against a wide range of insect pests. It has been evaluated against over 250 insect pests and on more than 60 crops worldwide. Fipronil, as marketed under the name Regent, has been used against lepidopteran and orthopteran pests on a wide range of field and horticultural crops and coleopteran larvae in soils. Fipronil acts on gamma amino butyric acid (GABA) receptor, the principal nerve transmitter in insects, preventing the inhibition of GABA. Biological studies have shown that fipronil interferes with the passage of chloride ions through the gamma amino butyric acid disrupting central nervous system (CNS) activity. Fipronil is very highly toxic for crustaceans, insect and zooplankton, as well as bees, termites, rabbits, the African tilapis, the fringe-toed lizard and certain groups of gallinaceous birds.

Microorganisms can be helpful when it comes to the elimination of pesticides. The increasing number of pesticides used in agriculture has recently acquired great importance due to the contamination of the environment. Microorganisms are of great importance in environmental cleaning and insecticide degradation. The bacterial *Paracoccus* sp. has been identified for the degradation of fipronil. *Paracoccus* sp. have been described as bacteria capable of utilizing carbon and nitrogen as source of energy from the fipronil. Cultures of *Orchrobacterium* sp., *Arthrobacter* sp. and *Burkholderia* sp. isolated and identified on the basis of 16s rDNA gene sequences, have shown in situ biodegradation of aendosulfan, a-endosulfan and b-endosulfan, respectively. In certain embodiments of the present invention, modifications can be brought about in certain microbes to encourage the organisms to degrade various pesticides at a faster rate. Such degradation by certain microbes can be achieved by introducing such microbes into the gut microbiome of particular insects such that such organisms can provide the benefits of degradation of particular insecticides in a manner that precludes the harm to the insect's health that would otherwise occur. In certain embodiments, *Paracoccus* sp. is employed to degrade fipronil. While introduction into the gut microbiomes of particular insects of particular bacteria and microbes known to degrade particular insecticides is one aspect of several embodiments of the present invention, other embodiments entail the incorporation of specific genes from organisms known to degrade particular pesticides such that those same pesticide degradation abilities are incorporated into the resident and native bacterial flora of particular insect gut microbiomes. This can be achieved without undue experimentation by one of ordinary skill in the art as the employment of CRISPR systems, in conjunction with knowledge of particular genomes of bacteria known to degrade certain pesticides, provides the requisite knowledge and guidance to effect particular genomic transformation and manipulation of host gut microbiomes such that degradation of pesticides by such bacteria is made possible. Specifically, there are acknowledged bacteria that possess the ability to degrade fipronil and the genomes of such bacteria are known. For example, the genome sequence of *Paracoccus* denitrificans strain ISTOD1 of 4.9 Mb has been elucidated and thus, one of skill in the art can readily employ CRISPR systems to manipulate and to incorporate the genes from such microbe involved in the degradation of fipronil so that the microbes resident in the gut microbiome of insects, and in particular of honey bees (but as described herein, also of monarch butterflies and bats, etc.), would then possess the ability to degrade pesticides, specifically fipronil, that are causing them such current harm. See e.g., Medhi, et. al, Genome Sequence of a Heterotrophic Nitrifier and Aerobic Denitrifier, *Paracoccus* denitrificans Strain ISTOD1, Isolated from Wastewater, Genome Announc. 2018 April; 6(15): e00210-18. See also, Kumar, et. al., Biodegradation of Fipronil by *Paracoccus* sp in Different Types of Soil, Bulletin of Environmental Contamination and Toxicology 88(5):781-7 (2012), both of which are incorporated herein by this reference.

In a similar manner as described herein, still other genomes of microbes may be employed to achieve the biodegradation of fipronil by gut microbes in particular insects, including the honeybee, for example: Degradation of fipronil by *Stenotrophomonasacidaminiphila*, Uniyal, et. al, Degradation of fipronil by *Stenotrophomonasacidaminiphila* isolated from rhizospheric soil of *Zea mays,* 3 Biotech. 2016 June; 6(1): 48; Mandal K, et. al, Microbial degradation of fipronil by *Bacillus thuringiensis*, Ecotoxicol Environ Saf. 2013 July; 93:87-92, also incorporated herein by this reference, as well as the following: Huang, et. al., Genome Sequencing and Comparative Analysis of *Stenotrophomonas acidaminiphila* Reveal Evolutionary Insights Into Sulfamethoxazole Resistance, Front Microbiol. 2018; 9: 1013.

The last few years have witnessed an unprecedented increase in the number of novel bacterial species that hold potential to be used for metabolic engineering. Historically, only a relatively few bacteria have attained the acceptance and widespread use in industrial bioproduction of compounds. Now, however, with the ability to perform targeted genome engineering of bacterial chassis, such as via CRISPR systems, synthetic biology is able to provide bacteria that can accomplish degradation of compounds in an unprecedented fashion.

Decades of research considerably expanded the repertoire of biological functions that microbial cells can incorporate into their physiological and metabolic agendas. Nowadays, designer cells can be constructed by adopting a combination of genome editing tools, chemical DNA synthesis and DNA assembly technologies—thereby fulfilling the practical goal of synthetic biology, that is, the construction of living cells from individual parts, which are purposefully assembled to yield a functional entity. As used herein, a biological chassis can be defined as the physical, metabolic and regulatory containment for plugging-in and plugging-out dedicated genetic circuits and regulatory devices. The integration of synthetic biology tools and strategies into advanced metabolic engineering has enabled the incorporation of a number of non-traditional microorganisms as hosts for developing efficient microbial cell factories. The (already extensive) list of the microbial hosts that can be adopted for such purposes continues to expand as more tools for precise gene and genome manipulation become available. Bacterial hosts traditionally employed in the production of useful products include *Escherichia coli, Bacillus subtilis, Streptomyces* sp., *Pseudomonas putida*, and *Corynebacterium glutamicum*, and for each there exists extensive background fundamental knowledge. In addition to these bacterial hosts, the present invention also includes the use of alternative hosts, some of which have been modified, such as via CRISPR systems. Building on the knowledge gained from the most used Gram-negative bacterial chassis, *E. coli*, and the Gram-positive bacterium *Bacillus subtilis*, the selection of other bacterial hosts for particular treatments of diseases will be readily determined by those of skill in the art due to the physical and genetic makeup and unique physiological and metabolic properties of microorganisms that are involved in specific diseases or conditions.

In the field of insect microbiomes, and in particular the gut microbiome of the honey bee, it is known that honeybees with compromised gut flora are malnourished and susceptible to infection. It is further acknowledged that as an herbicide, glyphosate works by blocking an enzyme called EPSP synthase in plants and microbes needed to create aromatic amino acids like phenylalanine and tryptophan. Glyphosate doesn't kill microbes, but it keeps them from growing, and most bacteria found in the gut of honey bees carry the gene for the enzyme. While some species of bacteria in the gut of honeybees are susceptible to glyphosate, others are less so because they carry a gene for a glyphosate-resistant version of EPSPS.

In certain embodiments of the present invention, the gut microbiome of the Monarch butterfly is manipulated so that it is able to at least partially degrade particular pesticides. In several embodiments, that pesticide is a neonicotinoid. In others, it is the pesticide fipronil. It is believed that certain pesticides are more rapidly eliminated from the monarch gut than others. For example, it is believed that fipronil is bioaccumulated by monarchs more than neonicotinoids. Employment of the present invention to inoculate the gut microbiomes of honeybees with bacteria engineered to degrade either or both a noenicitinoid or fipronil forms the basis of various embodiments of the present invention. The particular gut microbiomes of any particular creature are distinct, and as such one of skill in the art will appreciate that employing natively present microorganisms from any particular creature, such as a monarch butterfly, etc. should be assessed and modifications to such creatures microbiome (e.g. gut, skin, oral, etc.) should be the focus to address carrying out fipronil degradation. For example, the particular bacteria in the microbiomes of particular creatures can be manipulated and modified so as to express fipronil degradation genes in a manner that will not significantly harm the creature, but will degrade amounts of fipronil such that the creature will not die. One of skill in the art will appreciate the various microbes that can be modified, e.g. through CRISPR systems as described herein to accomplish desired rates and degrees of fipronil degradation.

In certain embodiments, a method for providing a Monarch butterfly with the ability to assimilate pesticides involves inoculating a monarch butterfly with a culture of pesticide degrading bacteria selected from the group consisting of: *L. rhamnosus* and *L. plantarum*, whether or not purposefully manipulated (via CRISPR systems) to include genes whose expression by the pesticide degrading bacteria results in the degradation of the pesticide, said pesticide degrading bacteria being modified to include such genes via the use of a clustered regularly interspaced short palindromic repeats (CRISPR) CRISPR associated protein (Cas) system or using a clustered regularly interspaced short palindromic repeats (CRISPR) from prevotella and francisella 1 (Cpf1) nuclease.

The microbes that inhabit the gut of monarch caterpillars are extremely low in abundance and predominantly leaf-derived. While not bound by theory, the present inventors believe that the high pH, simple gut structure, and fast transit times that typify caterpillar digestive physiology prevents microbial colonization. This forms one important aspect of several embodiments of the present invention, as instead of a focus on milkweed, the administration (or inoculation) of adult Monarchs with microbes able to degrade pesticides is believed to be effective in ceasing the decline of the Monarchs. In other embodiments, the population decline of Monarch butterflies may be tied to exposure to non-target pesticides on the common milkweed *Asclepias syriaca*, during larval development. But as noted, because the caterpillar gut does not possess many bacteria, it is believed that it is the microbiota of the adult Monarch butterfly that is important when it comes to the negative effects of pesticides on the survival and health of such butterflies. Indeed, studies have revealed that monarch declines have coincided with the increase in use of neonicotinoids throughout agricultural regions in their summer breeding habitat. Thus, one aspect of the present invention lies in the contention that it is not the presence of pesticides on milkweed that negatively affects the monarch, but rather, the effect of pesticides is instead directed to the inclusion of pesticides in the blooming plants that feed adult monarch butterflies. Sublethal effects of insecticides on butterflies are linked to reduced larval size, long development time, low mobility, minimal adult longevity, change in feeding behavior and immunology, and improper navigation and orientation.

Indeed, studies have shown no significant effects on immature development time and survival to the adulthood monarch butterfly, when just the larvae of monarchs were exposed to insecticides, whereas a reduction in wing length was observed for adult butterflies. Thus, in various aspects and embodiments of the present invention, providing the monarch butterfly with the ability to assimilate health degrading pesticides is focused on the non-larval stages of development. Thus, one important feature of the present invention relates to the application of suitable bacteria to an adult butterflies' gut is achieved so that such bacteria can degrade otherwise toxic pesticides, such as a variety of neonicotinoid pesticides as noted herein.

Certain embodiments of the present invention are therefore directed to a method for providing a Monarch butterfly with the ability to assimilate pesticides, such method involving administering and/or inoculating a Monarch butterfly with a culture of pesticide degrading bacteria, such pesticide degrading bacteria having genes whose expression results in the degradation of the pesticide. In various embodiments, such bacteria may be one or more of the following: *L. rhamnosus*, *Commensalibacter intestine*, *Commensalibacter papalotli*, *Lactobacillus paracasei*, *Bifidobacterium bifidum*, *Lactobacillus acidophilus*, *Lactococcus lactis*, *Bifidobacterium animalis*, *Lactobacillus thermophilus*, *Bacillus clausii*; *Lactobacillus plantarum*, *Leuconostoc citreum* and *Ochrobactrum intermedium*. In still other embodiments, a CRISPR-Cas9/CRISPR-Cpf1 system may be employed (which may be different from the natural CRISPR system in such bacteria or residing in a typical Monarch gut microbiome) to ameliorate pathogens in the Monarch butterfly gut.

Flowers at times host abundant and specialized communities of bacteria and fungi that influence floral phenotypes and interactions with pollinators. Ecological processes drive variation in microbial abundance and composition at multiple scales, including among plant species, among flower tissues, and among flowers on the same plant. Variation in microbial effects on floral phenotype suggests that microbial metabolites could cue the presence or quality of rewards for pollinators, but most plants are unlikely to rely on microbes for pollinator attraction or reproduction. From a microbial perspective, flowers offer opportunities to disperse between habitats, but microbial species differ in requirements for and benefits received from such dispersal. Floral microbes shape the evolution of floral traits, influence fitness of floral visitors, and respond to anthropogenic change. One aspect of the present invention relates to the ability of pollinators, especially bees and butterflies, and specifically honey bees and Monarch butterflies, to be inoculated with select microbes, and in particular bacteria that reside in the gut of Monarch butterflies, so as to enable the butterfly to degrade pesticides, such as neonicotinoid pesticides and/or fipronil, in a fashion that improves the health of such butterflies. Thus, these plant-pollinator interactions are a way to administer desired microbiota to insects in a fashion that is beneficial to such insects.

Thus, one aspect of the present invention is the recognition that while the milkweed is critical to the survival of Monarch butterflies, the preferred way to enable Monarchs to survive exposures to pesticides, such as neonicotinoids, is to administer select bacteria to plants other than milkweed to convey such microbes to Monarchs so that they are incorporated into the gut microbiome of the Monarchs, enabling the butterflies to degrade such pesticides. The gut of the monarch caterpillar is simply too transient to impact the health of adult Monarch butterflies. Therefore, the gut microbiome of adult butterflies requires administration of beneficial bacteria so that they can assimilate and degrade pesticides. As adult Monarchs feed off of flowers during their long sojourn, the application of beneficial bacteria to flowers that attract Monarchs is one aspect of various embodiments of the present invention. In other words, while planting milkweeds is important for the caterpillars to survive, the modification of the microbiome of flowers that attract Monarchs is the key to administering a sufficient amount of bacteria that can assist the Monarch in degrading pesticides that it may be exposed to. As described herein, modification of bacteria to have such abilities is part of the present invention and the employment of CRISPR systems is a preferred way to achieve the provision of beneficial bacteria that are of the same species as bacteria normally found in the gut microbiota of the Monarch. With such bacteria modified via CRISPR to have the capability of degrading pesticides, specifically neonicotinoids and fipronil, Monarch butterflies that visit flowers inoculated with such bacteria, have the opportunity of acquiring such bacteria such that degradation of existing or future pesticides can be accomplished, thus maintaining the health of the butterfly.

There is a strong overlap between microbiomes of flowers and bees and butterflies, suggesting that flowers are hubs of microbial transmission. It is believed that floral transmission is a driver of bee microbiome assembly, and florally sourced microbes shape both bee and butterfly microbiome content and provide transmission routes of microbes between hosts. Functionally, floral microbes provide benefits for bees and butterflies by enhancing nutritional quality, detoxification, and disintegration of pollen. Because flower microbes can also alter the attractiveness of floral resources, certain aspects of the invention are directed to enticing bees and/or butterflies, especially Monarchs, to flowers that have been administered (e.g. via spraying of microbes) a desired amount of microbes that serve to both attract and preferably to inoculate the pollinating insects. Together, these mechanisms affect the structure of the flower-bee-butterfly interaction network.

Indeed, various embodiments of the present invention administer effective amounts of microbes, especially bacteria and most preferably bacteria that have been altered using a CRISPR system to enable the bacteria to degrade pesticides, and preferably, neonicotinoid pesticides. Thus, honey bees may be utilized to effectively disseminate and distribute desired microbes and bacteria to flowers, which when later visited by butterflies, are able to be administered to the butterflies in a fashion such that the microbiome of the butterfly will then include the bacteria carried to the flower by the honeybee. Honeybees are particularly effective in this regard as because it is relatively easy to inoculate or administer to a bee hive (such as via bee boxes) with desired bacteria that have pesticide degradation abilities, the bees become vectors for the delivery of the same microbes and bacteria to flowers that butterflies will then visit, and when doing so, the butterflies will also be inoculated with such bacteria. This provides an effective way, that may be used instead of or in addition to microbe/bacterial spraying programs, to ensure that butterflies, especially the Monarchs, are exposed to effective amounts of bacteria such that the butterflies' gut microbiome is rendered capable of degrading pesticides, and especially neonicotinoid pesticides. As the adult Monarch butterfly is targeted by this bee-to flower vector approach, there is little need to address the treatment of milkweed to address the Monarch butterfly decline. Again, it is believed that the gut microbiomes of caterpillars of monarchs are so transitory that attempting to modify such gut microbiomes have little practical effect on saving monarchs. Conversely, however, without being bound by theory, the present inventors contend that employing bees to spread desired and preferably CRISPR-altered bacteria to flowers, it is possible to administer desired bacteria having desired traits and functionality so as to either enhance or disrupt the ability of other insects that visit flowers inoculated with such bacteria. In one instance, the ability of bees to inoculate flowers with desired bacteria that are able to degrade or detoxify pesticides is a method that can reduce the decline of monarch butterflies, as well as other insects who may visit such flowers and thereby become inoculated.

Floral nectar includes a diverse microbiome of yeasts and bacteria that depend on pollinators for dispersal. Plant species visited by the same set of pollinators support nectar microbial communities and thus, employing this knowledge, various embodiments of the present invention are directed to purposefully inoculating flowers with certain microbes so that such microbes are also exposed to certain pollinators, enabling the pollinators to have such microbes enhance their health, e.g. degrade pesticides that would otherwise adversely affect their health. In one embodiment, bees are employed to carry desired microbes to flowers, thus inoculating such flowers with the desired microbes, which are then transferred to butterflies and other insects when such butterflies/insects visit the flower. In other words, bees are employed as the entities that convey desired microbes so that butterflies that later visit such flowers are also inoculated with such microbes.

By the secretion of floral nectar rich in carbohydrates, flowers obtain pollinator services. Floral nectar hosts a diverse and dynamic microbiome of yeasts and bacteria that, once established, act to alter the floral environment and consequently the relationships with pollinators. This can include, e.g. reducing sugar concentration, modifying nectar carbohydrate and amino-acid compositions, and emitting volatiles, which is believed to have an effect on pollinator foraging preferences and success.

Microbes like yeasts and bacteria depend on insect vectors for their dispersal and establishment in nectar. The dominance of bacterial species within the Proteobacteria, especially species of Acinetobacter, Rosenbergiella and *Pseudomonas* is evident in the nectar microbiota. Individual flowers have diverse microbial communities that may or may not be similar to those found on other flowers. Pollinators visit specific sets of flowers and carry their own unique microbiota and flowers and pollinators share microbes. Thus, certain aspects of the present invention relate to assessing the microbiome of certain flowers and then administering thereto certain microbiota, such as modified bacteria, able to degrade pesticides so as to maintain the health of monarch butterflies and other pollinators. Whether such flower contact with desired microbiota is achieved via honey bees (preferred) or by other insects, the objective is to establish on flowers a different microbiome that can then be conveyed to select insects that visit such flowers.

Thus, certain embodiments of the present invention are directed to the inoculation of flowers by honey bees with desired bacteria that are able to degrade pesticides, such that when Monarch butterflies visit such flowers, they are exposed to such bacteria, transforming the microbiome of the Monarch butterflies so that pesticides can be degraded, thus enhancing the health of the Monarch butterflies.

One will appreciate that this Summary of the Invention is not intended to be all encompassing one of skill in the art will appreciate that the entire disclosure, as well as the incorporated references, provides a basis for the scope of the present invention as it may be claimed now and in future applications.

DETAILED DESCRIPTION OF PREFERRED EMBODIMENTS OF THE PRESENT INVENTION

Figure 1:
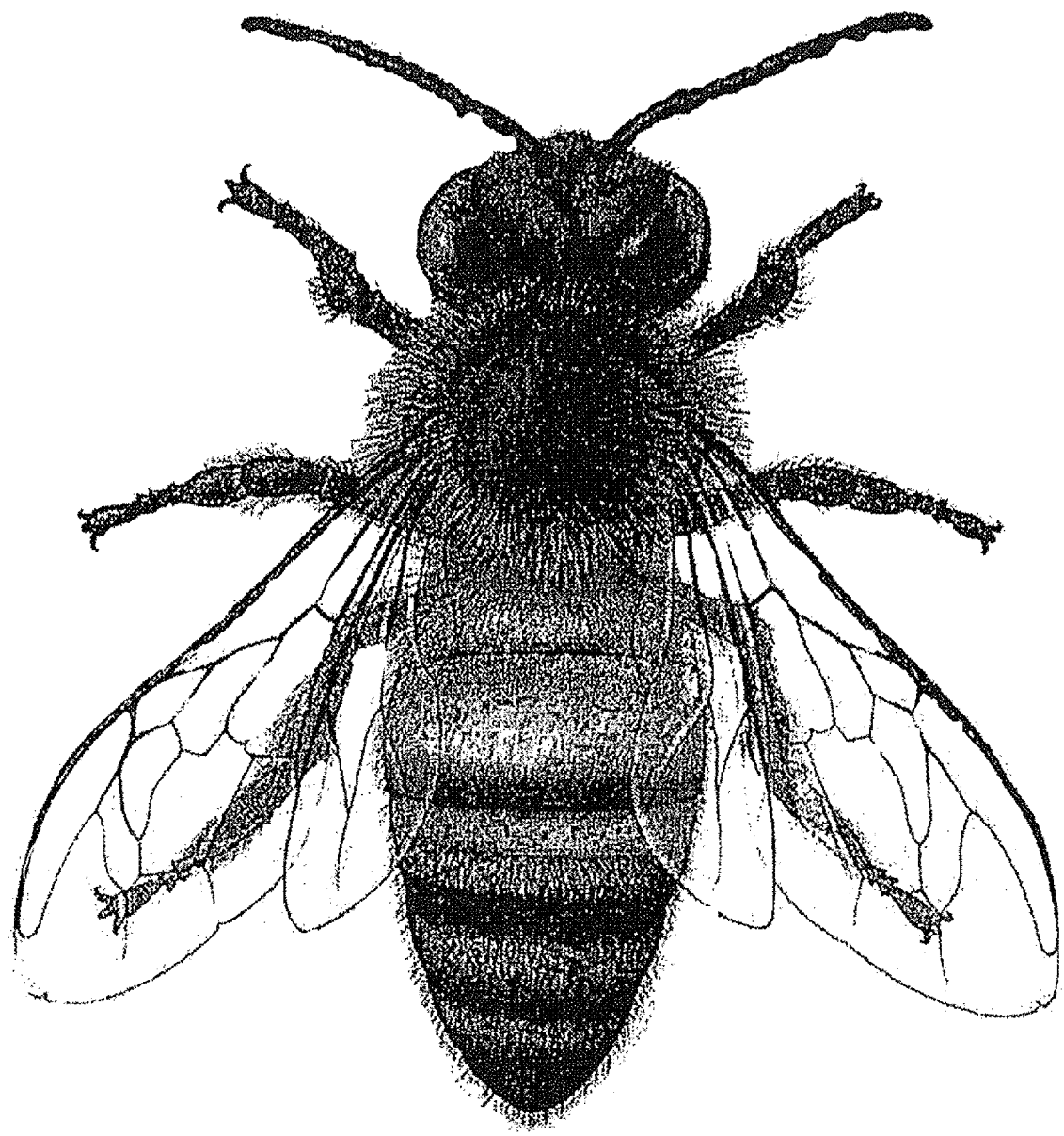
FIG. 1 is a depiction of a Monarch butterfly, which is also a pollinator that is assisted by employing the method and system of the present invention.
Figure 2:
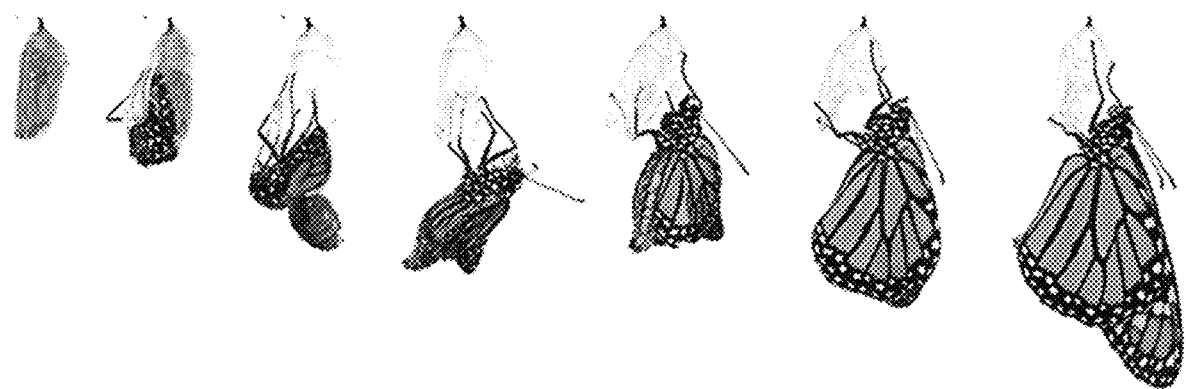
FIG. 2 shows the transformation of the monarch caterpillar from its chrysalis stage to emerge as a mature butterfly.
Figure 3:
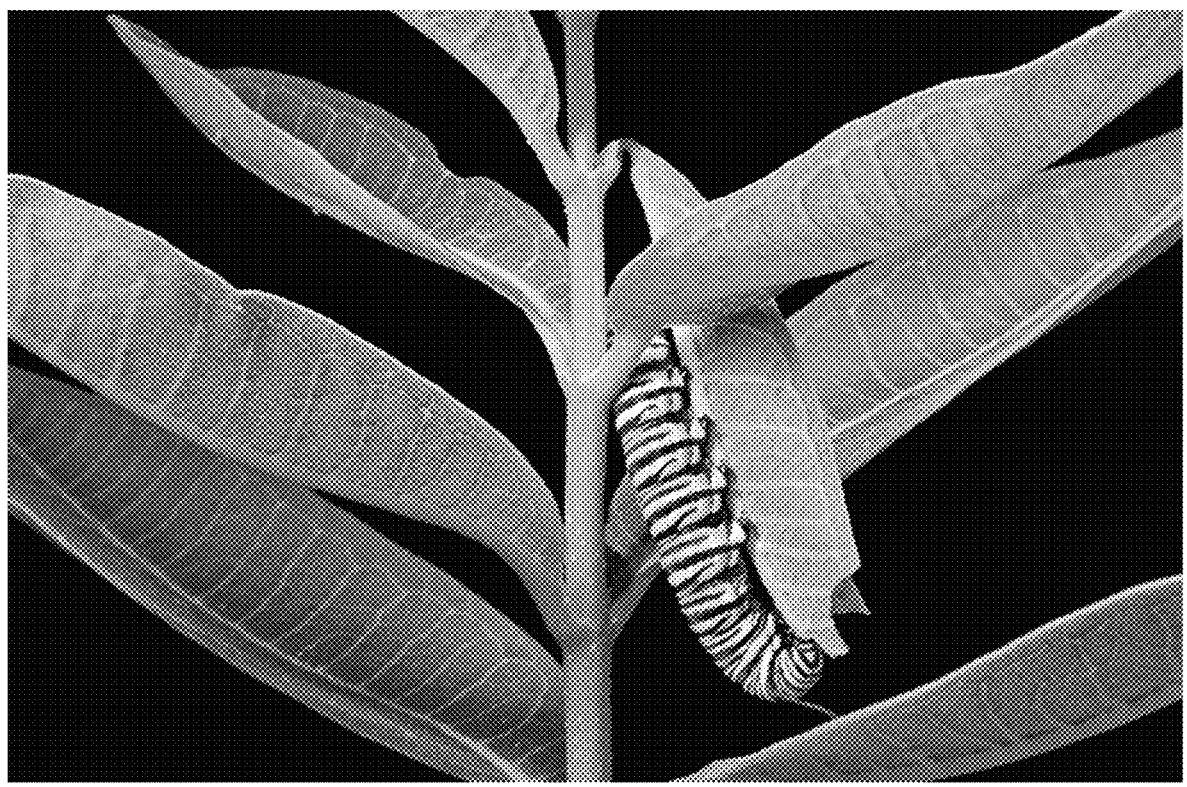
FIG. 3 shows a Monarch caterpillar feeding on milkweed.

It is believed that several neonicotinoid insecticides are implicated in the decline of Monarch butterfly populations, including the following: imidacloprid. clothianidin, thiamethoxam, and dinotefuran.

To provide necessary and sufficient written disclosure and enablement of the various embodiments of the present invention, the following references are incorporated by reference in their entireties: 20110269119 to Hutchinson, et al.; 20130064796 to Hamdi; 20140212520 to Del Vecchio, et al.; U.S. Pat. No. 9,017,718 to Tan; 20140065218 to Lang et al.; U.S. Pat. Nos. 6,599,883; 8,383,201; 5,158,789; 20070218114 to Duggan; 20040136923 to Davidson; U.S. Pat. No. 8,999,372 to Davidson; 20090196907 to Bunick; 20090196908 to Lee; 20030124178 to Haley; 20070293587 to Haley; 20100285098 to Haley; 2006-0204591 to Burrell; U.S. Pat. No. 7,087,249 to Burrelll; U.S. Pat. No. 6,210,699 to Acharya; U.S. Pat. No. 8,865,211 to Tzannis; 20140199266 to Park; U.S. Pat. No. 6,599,883 to Romeo; PCT/US2008/080362 to Dussia; 2007-0218114 to Duggan; 2004-0136923 to Davidson; 20110142942 to Schobel; 20040120991 to Gardner et al.; Fuchs et al. U.S. Pat. No. 4,136,162; 20040136923 to Davidson; U.S. Pat. No. 4,163,777 to Mitra; U.S. Pat. No. 5,002,970 to Eby, III; 20040096569 to Barkalow et al.; 20060035008 to Virgallito et al.; 20030031737 to Rosenbloom; U.S. Pat. No. 6,919,373 to Lam et al.; 20050196358 to Georglades et al.; U.S. Pat. No. 3,832,460 to Kosti; 2002002057 to Battey et al.; 20040228804 to Jones, et al.; U.S. Pat. No. 6,054,143 to Jones; U.S. Pat. No. 5,719,196 to Uhari; 20150150792 to Klingman; 20140333003 to Allen; 20140271867 to Myers; 20140356460 to Lutin; 20150038594 to Borges; U.S. Pat. No. 6,139,861 to Friedman; 20150216917 to Jones; 20150361436 to Hitchcock; 20150353901 to Liu; U.S. Pat. No. 9,131,884 to Holmes; 20150064138 to Lu; 20150093473 to Barrangou; 20120027786 to Gupta; 20150166641 to Goodman; 20150352023 to Berg; 20150064138 to Lu; 20150329875 to Gregory; 20150329555 to Liras; 20140199281 to Henn; US20050100559 (proctor and Gamble); 20120142548 to Corsi et al.; U.S. Pat. Nos. 6,287,610, 6,569,474, US20020009520, US20030206995, US20070054008; and U.S. Pat. No. 8,349,313 to Smith; and U.S. Pat. No. 9,011,834 to McKenzie; 20080267933 to Ohlson et al.; 20120058094 to Blasser et al.; U.S. Pat. No. 8,716,327 to Zhao; 20110217368 to Prakash et al.; 20140044734 to Sverdlov et al.; 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849; 20160348120 to Esvelt, et al., WO 2013026000 to Bryan and 20180020678 to Scharf et al. and Genomic signatures of honey bee association in an acetic acid symbiont, Smith et. al., bioRxiv preprint (Jul. 11, 2018).

While not bound by theory, it is believed that still other microbes may be employed in various embodiments of the present invention to address the objective of degrading neonicotinoid-like compounds, such bacteria showing an ability to degrade nicotine. The CRISPR-Cas system is employed to enable such modified species to degrade neonicotinoids. Thus, such system can be used to provide gut or skin bacteria that may grow on the bat skin or gut and can include genes that achieve desired degradation of neonicotinoids via the use of or presence of such genes in nicotine degrading organisms, such as *Agrobacterium tumefaciens* S33, *Apergillus oryzae, Pseudomonas putida* S16; *Arthrobacter nicotinovarans, Microsporum gypseum, Pellicularia filamentosa* JTS-208, *pseudomonas* sp. 41; *Microsporum gypseum; Pseudomonas* ZUTSKD; *Aspergillus oryzae* 112822; and *Ochrobactrum intermedium* DN2.

Microbial symbionts are important for host organisms, and insects rely on the communities of microorganisms in their guts for several functions. Hosts have evolved a range of mechanisms to protect themselves against parasites that are a large threat to their fitness. These defenses can extend beyond intrinsic host immunity and incorporate aspects of the environment in which host and parasite interact. Monarch butterfly (*Danaus plexippus*) larvae actively consume milkweeds (*Asclepias* spp.) that contain secondary chemical compounds, named cardenolides, which reduce parasite infection and virulence.

*Commensalibacter* is a genus of acetic acid bacteria and 16S rRNA gene sequences related to the *Commensalibacter* genus have been recovered from the guts of *Drosophila* species, honey bees, and bumble bees, as well as from Heliconius erato butterflies. The type strain *Commensalibacter intestini* A911 was isolated from *Drosophila* intestines, and the genome sequence of a *Commensalibacter* symbiont isolated from a monarch butterfly has been reported. *Commensalibacter papalotli* strain MX01, was isolated from the intestines of an overwintering monarch butterfly. The 2,332,652-bp AT-biased genome of *C. papalotli* MX01 is the smallest genome for a member of the Acetobacteraceae.

In certain embodiments, *Commensalibacter* bacteria are modified to render them able to degrade neonicotinoid insecticides and such bacteria are then purposefully provided to the gut biome of monarch butterflies to enable the butterflies to degrade such pesticides, and thus survive and remain viable for reproduction. In a particular embodiment, the genes responsible for the ability to degrade neonicotinoids are derived from the *Ochrobactrum intermedium* SCUEC4 strain, wherein the preservation number is CCTCC NO:M2014403; and/or *Ochrobactrum intermedium* strain LMG3306.

CRISPR systems may be employed to insert desired genes into various bacteria that can survive in the gut of the monarch butterfly such that these microbes can degrade particular insecticides, including neonicotinoids.

One aspect of the present invention is directed to improving monarch butterfly fitness by modifying the monarch butterfly microbiome, either by incorporation of select species of bacteria into existing gut microbiomes of the monarch butterfly, or by incorporation of genetic elements into existing bacteria within a monarch butterfly's gut such that the modified microbe is able to degrade neonicotinoids. These engineered microbiomes are purposefully designed to have with specific beneficial effects on the host monarch butterfly fitness. Thus, by employing host-mediated microbiome selection, one is able to select and modify microbial communities indirectly through the host, thus influencing the monarch butterfly microbiome and positively affecting monarch butterfly fitness. The methods that may be used to impose artificial selection on the monarch butterfly microbiome include various techniques known to those of skill in the art, including CRISPR-Cas and Cpl1 systems. Thus, particular cultures of particular microbes can be purposefully included into monarch butterfly populations so as to inhabit their gut microbiome, and by doing so, provide the monarch butterflies with the ability to degrade neonicotinoids. Other embodiments are directed to engineering a modification of the monarch butterfly gut microbes that do not already possess such neonicotinoid degradation genes.

Detoxification gene inventory reduction may reflect an evolutionary history of consuming relatively chemically benign nectar and pollen. Thus, certain embodiments are directed to the development of predictable microbiome-based biocontrol strategies by providing the ability of monarch butterflies to degrade or otherwise assimilate insecticides or other chemical agents, including neonicotinoids. Such a novel biocontrol strategy can not only be used to suppress pathogens, but can also be effectively used to establish microbiomes in a desirable beneficial composition for particular purposes.

In certain embodiments, xenobiotic detoxification is employed to address the problems associated with monarch butterfly health. In particular embodiments, the conversion of lipid-soluble substances to water-soluble, excretable metabolites is achieved. In a primary detoxification step, a toxin structure is enzymatically altered and rendered unable to interact with lipophilic target sites. Such functionalization is affected primarily by cytochrome P450 monooxygenases (P450) and carboxylesterases (CCE), although other enzymes, including flavin-dependent monooxygenases and cyclooxygenases may also be employed. Further reactions typically involve conjugation of products of the above referenced step to achieve detoxification for solubilization and transport. Glutathione-S-transferases (GST) are the principal enzymes used, although other enzymes in insects may include glycosyltransferases, phosphotransferases, sulfotransferases, aminotransferases, and glycosidases. Nucleophilic compounds can be rendered hydrophilic by UDP-glycosyltransferases. The final stage of detoxification involves transport of conjugates out of cells for excretion. Among the proteins involved in this process are multidrug resistance proteins and other ATP-binding cassette transporters.

Any one or more of appropriate bacteria can be modified to express particular genes that have been shown (for example by its inclusion in the bacteria *Ochrobactrum intermedium*) to degrade neonicotinoids in a manner that preserves monarch butterfly health. One of skill in the art can address compatibility issues with respect to the use of such bacteria and can make modifications thereto to render it tolerable and viable in the gut microbiome of the monarch butterfly. Genetic modification of existing microbes in the monarch butterfly gut can also be performed to render such native bacteria able to produce agents effective in degrading neonicotinoids.

Impacts to monarch butterflies from sublethal exposure to neonicotinoids, such as imidacloprid, especially in the presence of other stressors, is believed to result in severe and significant dysfunctions within and have an adverse impact on monarch colony health and to the immune function in individual monarch butterflies. It is believed that several neonicotinoid insecticides are implicated in the decline of monarch butterfly populations, including the following: imidacloprid. clothianidin, thiamethoxam, and dinotefuran.

In particular embodiments, the present invention is directed to a system and method used for the biological control of the welfare of monarch butterflies, and for prophylaxis and treatment of pathological disorders of monarch butterflies caused by insecticides, and especially neonicotinoids. In certain embodiments, bacteria are modified, preferably via the CRISPR-Cas system, and such bacteria are then provided to monarch butterflies in a fashion such that they can reside in the gut of the monarch butterfly, such bacteria selected from the group consisting of one or more bacteria in six bacterial families: the Acetobacteraceae (Alphaproteobacteria), Moraxellaceae and Enterobacteriaceae (Gamma proteobacteria), Enterococcaceae and Streptococcaceae (Firmicutes), and an unclassified family in the Bacteroidetes phylum. In particular embodiments, the bacteria employed in the present invention include one or more of the following: *Commensalibacter*, and in particular *Commensalibacter intestini* A911 and *Commensalibacter papalotli* strain MX01; *Lactobacillus paracasei* ssp., *Bifidobacterium bifidum, Lactobacillus acidophilus, Lactococcus lactis, Bifidobacterium animalis, Lactobacillus thermophilus*, and *Bacillus clausii; Lactobacillus plantarum* YML001, *Lactobacillus plantarum* YML004 and *Leuconostoc citreum* KM20; *Ochrobactrum intermedium* SCUEC4 strain, wherein the preservation number is CCTCC NO:M2014403; *Ochrobactrum intermedium* strain LMG3306. Particularly preferred microbes to employ, whether for extraction of their neonicotinoid genes for transplantation into the gut microbes of monarch butterflies, or for the microbes inclusion as a microbe in the gut of monarch butterflies, is a member of the genus *ochrobactrum*, in the alpha-2 subgroup of the domain Proteobacteria.

Modifying the gut microbiota of monarch butterflies to provide them with the ability to consume chemically defended plants can thus be achieved by varying the monarch butterflies associated microbial communities. Different microbes may be differentially able to detoxify compounds toxic to the monarch or may be differentially resistant to the potential antimicrobial effects of some compounds.

In certain embodiments, the administration of effective bacteria that can beneficially assist monarch butterflies in combating the ill effects of neonicotinoids can be achieved in many ways, including but not limited to spraying colonies of butterflies or caterpillars that will emerge as butterflies with bacterial solutions; providing such bacterial solutions in places where monarch butterflies frequent in a manner that they will be exposed to the same, such as by having bacteria provide in sweetened solutions that monarch butterflies are drawn to; purposeful capture and inoculation of members of a colony such that they will be able to then spread the bacteria to other bats in a colony, effectively inoculating an entire colony of monarch butterflies.

As one of skill in the art of living will appreciate, the reason to preserve nature is not merely within the realm of science, as beauty and literature are rooted in those creatures who share this earth with us. The philosophers of the past recognized this fact. Nietzsche once said: “And to me also, who appreciate life, the butterflies, and soap-bubbles, and whatever is like them amongst us, seem most to enjoy happiness.” Our treasure lies in the beehive of our knowledge. We are perpetually on the way thither, being by nature winged insects and honey gatherers of the mind.” Aristotle chimed in: “As the eyes of bats are to the blaze of day, so is the reason in our soul to the things which are by nature most evident of all.” Karl von Frisch said “Nature has unlimited time in which to travel along tortuous paths to an unknown destination. The mind of man is too feeble to discern whence or whither the path runs and has to be content if it can discern only portions of the track, however small.” So as Nabokov suggested, “do what only a true artist can do . . . pounce upon the forgotten butterfly of revelation.” “Literature and butterflies are the two sweetest passions known to man.”

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception, upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method for providing a Monarch butterfly with the ability to assimilate pesticides, comprising, inoculating a Monarch butterfly with a culture of pesticide degrading bacteria, wherein the pesticide degrading bacteria include genes whose expression by the pesticide degrading bacteria results in the degradation of the pesticide, said pesticide degrading bacteria being modified to include said genes using a clustered regularly interspaced short palindromic repeats (CRISPR) CRISPR associated protein (Cas) system or using a clustered regularly interspaced short palindromic repeats (CRISPR) from *prevotella* and *francisella* 1 (Cpf1) nuclease, said pesticide degrading bacteria selected from the group consisting of *L. rhamnosus* and *L. plantarum*.

2. The method as set forth in claim 1, wherein said genes express cytochrome P450 enzymes.

3. The method as set forth in claim 1, wherein said genes comprise P450 genes of the CYP6 and CYP3 clade.

4. The method as set forth in claim 1, wherein said inoculating comprises spraying a Monarch butterfly with said pesticide degrading bacteria.

5. The method as set forth in claim 1, wherein said inoculating comprises providing the pesticide degrading bacteria in a sweetened solution.

6. The method as set forth in claim 1, wherein the pesticide comprises a neonicotinoid insecticide.

7. The method as set forth in claim 1, further comprising employing a different CRISPR-Cas9/CRISPR-Cpf1 to ameliorate pathogens in the Monarch butterfly gut.

8. A method for providing a Monarch butterfly with the ability to assimilate pesticides, comprising, inoculating a Monarch butterfly with a culture of pesticide degrading bacteria, wherein the pesticide degrading bacteria include genes whose expression by the pesticide degrading bacteria results in the degradation of the pesticide, said pesticide degrading bacteria selected from the group consisting of *L. rhamnosus* and *L. plantarum*.

9. The method as set forth in claim 8, wherein said inoculating comprises one of providing the pesticide degrading bacteria in a sweetened solution, spraying a Monarch butterfly with said pesticide degrading bacteria, and having a honey bee inoculate a flower with the pesticide degrading bacteria.

10. The method as set forth in claim 8, wherein said pesticide degrading bacteria is modified to include said genes using a clustered regularly interspaced short palindromic repeats (CRISPR) CRISPR associated protein (Cas) system or using a clustered regularly interspaced short palindromic repeats (CRISPR) from *prevotella* and *francisella* 1 (Cpf1) nuclease, and wherein said genes express cytochrome P450 enzymes.

11. The method as set forth in claim 8, further comprising employing CRISPR-Cas9/CRISPR-Cpf1 to delete antibiotic resistance genes transferred to pathogenic bacteria in the Monarch butterfly gut.

12. The method as set forth in claim 8, further comprising employing a CRISPR-Cas9/CRISPR-Cpf1 to ameliorate pathogens in the Monarch butterfly gut.

13. A method for providing a Monarch butterfly with the ability to assimilate pesticides, comprising, providing a Monarch butterfly with a culture of pesticide degrading bacteria, wherein the pesticide degrading bacteria include genes whose expression by the pesticide degrading bacteria results in the degradation of the pesticide, said pesticide degrading bacteria selected from the group consisting of *L. rhamnosus, Commensalibacter intestine, Commensalibacter papalotli, Lactobacillus paracasei, Bifidobacterium bifidum, Lactobacillus acidophilus, Lactococcus lactis, Bifidobacterium animalis, Lactobacillus thermophilus, Bacillus clausii; Lactobacillus plantarum, Leuconostoc citreum* and *Ochrobactrum intermedium*.

14. The method as set forth in claim 13, wherein said genes express cytochrome P450 enzymes.

15. The method as set forth in claim 13, wherein said genes comprise P450 genes of one of the CYP6 and CYP3 clades.

16. The method as set forth in claim 13, wherein said genes are selected from the group consisting of a CYP353D1v2 gene and a SCL3-10 nitrile hydratase beta subunit gene.

17. The method as set forth in claim 13, further comprising employing CRISPR-Cas9/CRISPR-Cpf1 to delete antibiotic resistance genes transferred to pathogenic bacteria in the Monarch butterfly gut.

18. The method as set forth in claim 13, further comprising improving Monarch butterfly fitness by modifying the Monarch butterfly microbiome by using CRISPR-Cas9/CRISPR-Cpf1 to select and modify microbial communities to positively affect Monarch butterfly fitness.

19. The method as set forth in claim 13, wherein said pesticide degrading bacteria comprises *L. rhamnosus*.

20. The method as set forth in claim 13, further comprising employing a CRISPR-Cas9/CRISPR-Cpf1 to ameliorate pathogens in the Monarch butterfly gut.

* * * * *